United States Patent [19]
Durette et al.

[11] Patent Number: 5,104,862
[45] Date of Patent: Apr. 14, 1992

[54] BETHALACTAM ELASTASE INHIBITORS CONTAINING PHOSPHOROUS ACID DERIVATIVES AT THE 4-POSITION OF THE 2-AZETIDINONE

[75] Inventors: Philippe L. Durette, New Providence; Malcolm Maccoss, Freehold, both of N.J.

[73] Assignee: Merck & Co., Inc., Rahway, N.J.

[21] Appl. No.: 672,227

[22] Filed: Mar. 20, 1991

[51] Int. Cl.$^5$ .................... C07F 9/568; A61K 31/675
[52] U.S. Cl. .................... 514/79; 540/360; 514/851
[58] Field of Search ............ 540/360; 514/79

[56] References Cited

U.S. PATENT DOCUMENTS

| | | | |
|---|---|---|---|
| 4,064,120 | 12/1977 | Krapcho et al. | 544/111 |
| 4,115,382 | 9/1978 | Krapcho et al. | 544/111 |
| 4,166,907 | 9/1979 | Krapcho et al. | 544/111 |
| 4,174,317 | 11/1979 | Krapcho | 544/111 |
| 4,260,743 | 4/1981 | Bose | 546/275 |
| 4,493,839 | 1/1985 | Doherty et al. | 424/274 |
| 4,510,086 | 4/1985 | Ross et al. | 540/360 |
| 4,534,896 | 8/1985 | Treuner et al. | 514/210 |
| 4,559,335 | 12/1985 | Zahler | 514/210 |
| 4,576,749 | 3/1986 | Zahler et al. | 544/310 |
| 4,680,391 | 7/1987 | Firestone et al. | 540/355 |

FOREIGN PATENT DOCUMENTS

| | | |
|---|---|---|
| 295547 | 5/1971 | Austria . |
| 375640 | 9/1981 | Austria . |
| 0023097 | 1/1981 | European Pat. Off. . |
| 0042026 | 12/1981 | European Pat. Off. . |
| 0076621 | 4/1983 | European Pat. Off. . |
| 0199630 | 10/1986 | European Pat. Off. . |
| 0337549 | 10/1989 | European Pat. Off. . |
| 1945542 | 3/1971 | Fed. Rep. of Germany . |
| 2046822 | 3/1972 | Fed. Rep. of Germany . |
| 2046823 | 3/1972 | Fed. Rep. of Germany . |
| 2748827 | 3/1978 | Fed. Rep. of Germany . |
| 2824554 | 12/1978 | Fed. Rep. of Germany . |
| 2842466 | 4/1979 | Fed. Rep. of Germany . |
| 2911589 | 9/1979 | Fed. Rep. of Germany . |
| 3007298 | 3/1987 | Fed. Rep. of Germany . |
| 1192952 | 5/1970 | United Kingdom . |
| 1604752 | 12/1981 | United Kingdom . |
| 2093839 | 9/1982 | United Kingdom . |

OTHER PUBLICATIONS

Yoshifuji, Chem. Abstracts, vol. 105, Abs. 97895t (1986).
Peitsch, Hartmut, Tetrahedron Letters, No. 45, pp. 4053–4056 (1976).
Tanaka et al., Heterocycles, vol. 24, No. 9, pp. 2539–2543 (1986).

*Primary Examiner*—Mark L. Berch
*Attorney, Agent, or Firm*—Curtis C. Panzer; Hesna J. Pfeiffer

[57] ABSTRACT

New substituted azetidinones of the general formula (A), which have been found to be potent elastase inhibitors and thereby useful as anti-inflammatory and antidegenerative agents, are described.

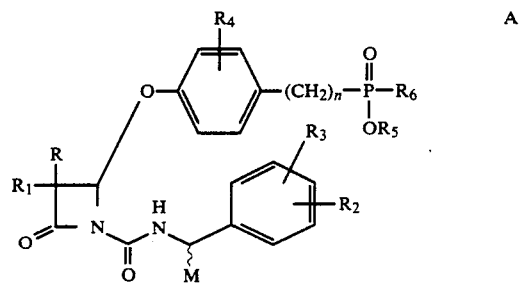

13 Claims, No Drawings

BETHALACTAM ELASTASE INHIBITORS CONTAINING PHOSPHOROUS ACID DERIVATIVES AT THE 4-POSITION OF THE 2-AZETIDINONE

BACKGROUND OF THE INVENTION

We have found that a group of new substituted azetidinones are potent elastase inhibitors and therefore are useful anti-inflammatory and antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis, atherosclerosis, sepsis, septicemia, shock, periodontitis, cystic fibrosis and acute respiratory distress syndrome.

The role of proteases from granulocytes, leukocytes or macrophages is related to a rapid series of events which occur during the progression of an inflammatory condition:

(1) There is a rapid production of prostaglandins (PG's) and related compounds synthesized from arachidonic acid. This PG synthesis has been shown to be inhibited by aspirin-related nonsteroidal anti-inflammatory agents, including indomethacin and phenylbutazone. There is some evidence that protease inhibitors prevent PG production;

(2) There is also a change in vascular permeability which causes a leakage of fluid into the inflammed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl-benzisothiazolones and their respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN's). It has been known that a variety of proteases are released from the macrophages and PMN's, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis, etc.

Elastase is one of these proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74-88). For example, one of the natural inhibitors, $\alpha_1$-antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, New York, pp. 196-206, 1979.

BRIEF DESCRIPTION OF THE INVENTION

The instantly claimed invention is directed to specifically substituted azetidionones in which the substituent in the 4-position is a substituted phenoxy moiety wherein the substituent is a phosphoric acid derivative and the N-substiuent is a phenylalkylaminocarbonyl group. This invention is also directed to pharmaceutical compositions and methods of using these specifically substituted azetidinones.

DETAILED DESCRIPTION OF THE INVENTION

This invention relates to potent elastase inhibitors of Formula A which are useful in the prevention, control and treatment of inflammatory and degenerative conditions especially arthritis and emphysema.

In one embodiment the instant invention is directed to the compounds of the Formula (A)

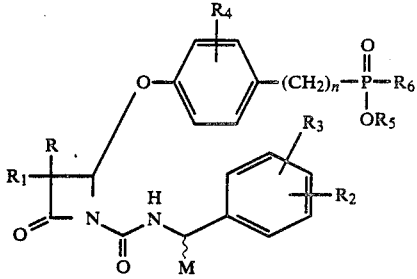

and pharmaceutically acceptable salts thereof wherein

R is H, $C_{1-6}$ alkyl, or $C_{2-6}$ alkenyl;

$R_1$ is H, $C_{1-6}$ alkyl, $C_{2-6}$ alkenyl or $C_{1-6}$ alkoxy-$C_{1-6}$ alkyl;

M is
(1) hydrogen,
(2) $C_{1-6}$ alkyl,
(3) hydroxy $C_{1-6}$-alkyl,
(4) halo $C_{1-6}$-alkyl,
(5) $C_{2-6}$ alkenyl, or
(6) $C_{1-6}$ alkoxy-$C_{1-6}$ alkyl;

$R_2$ and $R_3$ are each independently
(1) hydrogen,
(2) $C_{1-6}$ alkyl,
(3) halo,
(4) carboxy,
(5) $C_{1-6}$ alkoxy,
(6) phenyl,
(7) $C_{1-6}$ alkylcarbonyl,
(8) $C_{1-6}$ alkyloxycarbonyl,
(9) di-($C_{1-6}$alkyl)amino,
(10) phenoxy, or $R_2$ and $R_3$ are joined together to form a ring selected from furan, thiophene, and dioxacyclopentane;

$R_4$ is
(a) hydrogen,
(b) $C_{1-6}$ alkyl,
(c) halo, or
(d) $C_{1-6}$ alkoxy;

n is 0, 1, 2, 3, or 4;

$R_5$ is
(1) hydrogen,
(2) $C_{1-6}$ alkyl,
(3) $C_{6-10}$ aryl wherein the aryl group is selected from the group consisting of
(a) phenyl,
(b) napthyl,
(c) pyridyl,
(d) furyl,
(e) pyrryl,
(f) thienyl,
(g) imidazolyl,
(h) benzimidazolyl,
(i) pyrazinyl,
(j) pyrimidyl,
(k) quinolyl,
(l) isoquinolyl,
(m) benzofuryl, and
(n) benzothienyl, and mono and di-substituted $C_{6-10}$ aryl as defined above in items (a) to (n) wherein the substituents are independently $C_{1-6}$ alkyl, halo, hydroxy, $C_{1-6}$ alkyloxy, $C_{1-6}$ alkylcarbonyl, or $C_{1-6}$ alkoxy-$C_{1-6}$ alkyl; or (4) $C_{1-6}$ alkylcarbonyloxy-$C_{1-6}$ alkyl;

$R_6$ is
(a) hydrogen,
(b) $C_{1-6}$ alkyl,
(c) $C_{2-6}$ alkenyl,
(d) substituted $C_{1-6}$ alkyl wherein the substituent is halo, hydroxy, $C_{1-6}$ alkoxy, $C_{1-6}$ alkylcarbonyloxy, amino $C_{1-6}$ alkylamino, di-($C_{1-6}$ alkyl)amino, or tri-($C_{1-6}$ alkyl) ammonium,
(e) $C_{6-10}$ aryl wherein the aryl group is selected from the group consisting of
(1) phenyl,
(2) naphthyl,
(3) pyridyl,
(4) furyl,
(5) pyrryl,
(6) thienyl,
(7) imidazolyl,
(8) benzimidazolyl,
(9) pyrazinyl,
(10) pyrimidyl,
(11) quinolyl,
(12) isoquinolyl,
(13) benzofuryl, and
(14) benzothienyl, and mono and di-substituted $C_{6-10}$ aryl as defined above in items (1) to (14) wherein the substituents are independently $C_{1-6}$ alkyl, halo, hydroxy, $C_{1-6}$ alkyloxy, $C_{1-6}$ alkylcarbonyl, and $C_{1-6}$ alkoxycarbonyl.

In one class of this embodiment, the instant invention concerns compounds of Formula A and pharmaceutically acceptable salts thereof wherein M, R, and $R_1$ are each independently $C_{1-6}$ alkyl or $C_{2-6}$ alkenyl;

$R_2$ and $R_3$ are each independently hydrogen, $C_{1-6}$ alkyl, $C_{1-6}$ alkoxy, or $R_2$ and $R_3$ are joined together to form a ring selected from furan, thiophene, or dioxacyclopentane;

$R_4$ is hydrogen, $C_{1-6}$ alkyl, fluoro or chloro;

n is 0 or 1;

$R_5$ is hydrogen, $C_{1-6}$ alkyl or
$C_{1-6}$-alkylcarbonyloxy-$C_{1-6}$ alkyl; and $R_6$ is hydrogen, $C_{2-6}$ alkenyl, $C_{1-6}$ alkyl, or $C_{6-10}$ aryl.

One subclass of this embodiment concerns compounds of Formula A wherein:

M, R and $R_1$ are each independently $C_{1-6}$ alkyl;

$R_2$ is hydrogen, and $R_3$ is $C_{1-6}$ alkyl, $C_{1-6}$ alkyloxy, or $R_2$ and $R_3$ are joined together to form a ring selected from furan or dioxacyclopentane;

$R_4$ is hydrogen, $C_{1-6}$ alkyl, fluoro, or chloro;

n is 0 or 1;

$R_5$ is hydrogen, $C_{1-6}$ alkyl or
$C_{1-6}$-alkylcarbonyloxy-$C_{1-6}$ alkyl; and $R_6$ is hydrogen, $C_{1-6}$ alkyl, or $C_{6-10}$ aryl.

A narrower sub-class of this embodiment concerns compounds of Formula A wherein:

M is n-propyl;

R and $R_1$, are ethyl;

n is 0 or 1;

$R_2$ is hydrogen, and

R₃ is methyl, or methoxy, or R₂ and R₃ are joined together to form a ring selected from furan or dioxacyclopentane;

R₅ is hydrogen or $C_{1-6}$-alkylcarbonyloxy-$C_{1-6}$alkyl; and

R₆ is hydrogen, $C_{1-6}$ alkyl or $C_{6-10}$ aryl.

Exemplifying this class of the invention are the following:

A compound which is (4S)-3,3-Diethyl-1-[(R)-α-n-propyl-(4-methyl)benzylaminocarbonyl]-4-[4-(phenyl(hydroxyphosphinyl)methyl)-phenoxy]azetidin-2-one.

A compound which is (4S)-3,3-Diethyl-1-[(R)-α-n-propyl-(4-methyl)benzylaminocarbonyl]-4-[4-(allyl(ethoxyphosphinyl)methyl)-phenoxy]azetidin-2-one.

A compound which is (4S)-3,3-Diethyl-1-[(R)-α-n-propyl-(4-methyl)benzylaminocarbonyl]-4-[4-(methyl(ethoxyphosphinyl)methyl)-phenoxy]azetidin-2-one.

A compound which is (4S)-3,3-Diethyl-1-[(R)-α-n-propyl-(4-methyl)-benzylaminocarbonyl]-4-[4-(phenyl(ethoxyphosphinyl)methyl)-phenoxy]-azetidin-2-one.

A compound which is (4S)-3,3-Diethyl-1-[(R)-α-n-propyl-(4-methyl)-benzylaminocarbonyl]-4-[4-(allyl(hydroxyphosphinyl)methyl)-phenoxy]-azetidin-2-one.

A compound which is (4S)-3,3-Diethyl-1-[(R)-α-n-propyl-(4-methyl)-benzylaminocarbonyl]-4-[4-(methyl(hydroxyphosphinyl)methyl)-phenoxy]azetidin-2-one.

A compound which is (4S)-3,3-Diethyl-1-[(R)-α-n-propyl-(4-methyl)-benzylaminocarbonyl]-4-[4-(n-propyl(ethoxyphosphinyl)methyl-phenoxy]azetidin-2-one.

A compound which is (4S)-3,3-Diethyl-1-[(R)-α-n-propyl-(4-methyl)benzylaminocarbonyl]-4-[4-(n-propyl(hydroxyphosphinyl)methyl)-phenoxy]azetidin-2-one.

A compound which is (4S)-3,3-Diethyl-1-[(R)-α-n-propyl-(4-methyl)benzylaminocarbonyl]-4-[4-(n-propyl-(2-methyl-1-ethylcarbonyloxy-n-propoxyphosphinyl)methyl)-phenoxy]azetidin-2-one.

The compounds of the invention are prepared by the following representative schemes:

As shown in Scheme I, the phosphinic acid analogs were synthesized from the corresponding carboxylic acid 1 (prepared as described in EPO 337,549, published Oct. 18, 1989) by initial formation of the benzyl bromide 2 using BMS/THF (bromine-methylsulfide/tetrahydrofuran) followed by Br₂/Ph₃P (bromine/trimethylphosphine) in acetonitrile. The benzyl bromide 2 was then treated with the appropriate dialkyl alkylphosphonite in a Michaelis-Arbuzov reaction at 75°–125° C. to give the phosphinic acid esters 3. The corresponding free acids 4 were obtained by cleavage of the alkyl ester group with a halo-trimethylsilane, such as bromotrimethylsilane. The alkylphosphonites needed in the above mentioned Michaelis-Arbuzov reaction were prepared by reaction of the appropriate Grignard reagent with diethyl chlorophosphite.

The alkylcarbonyloxyalkyl esters of 4 were prepared by alkylation of the free phosphinic acids 4 with a 1-haloalkyl alkanoate, such as 1-chloroisobutyl propionate as shown in scheme I, in a solvent such as methylene chloride or chloroform, in the presence of a base, such as pyridine, triethylamine, N,N-diisopropylethylamine, and the like, and an alkali iodide, such as sodium or potassium iodide, and tetra-n-butylammonium hydrogensulfate.

SCHEME I

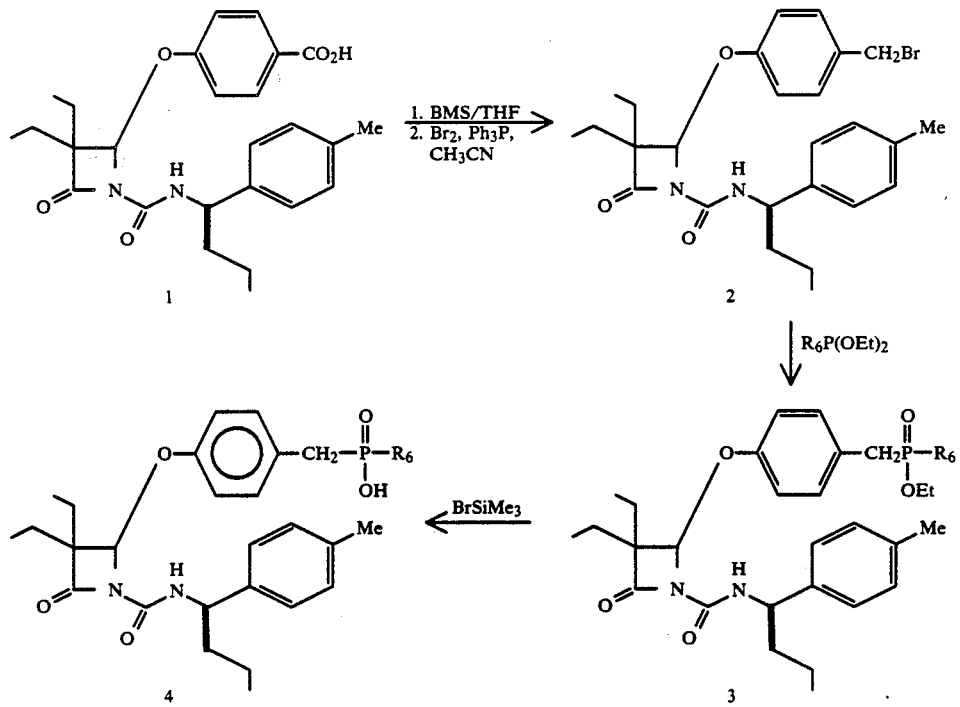

-continued
SCHEME I

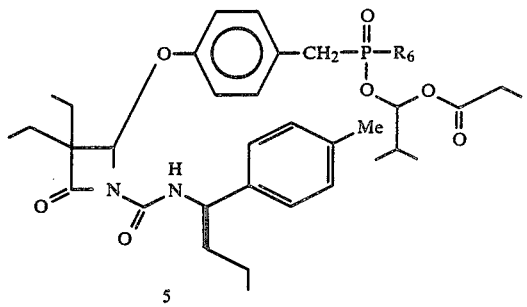

5

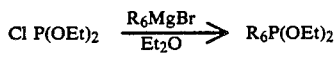

This invention also relates to a method of treating inflammation in patients using a compound of Formula A.

It has been found that the compounds of, Formula A are effective inhibitors of the proteolytic function of human granulocyte elastase as shown below:

TABLE I

| $R_6$ | $R_5$ | $k_{obs}/I$ ($M^1$ sec$^{-1}$) |
|---|---|---|
| phenyl | H | 1,200,000 |
| $CH_2CH=CH_2$ | Et | 1,300,000 |
| $CH_2CH=CH_2$ | H | 740,000 |
| $CH_2CH_2CH_3$ | H | 910,000 |
| $CH_3$ | H | 420,000 |

$k_{obs}/I$ ($M^{-1}$ sec$^{-1}$) is the second order rate constant in per mole per second for inactivation of the enzyme.

Enzyme Assays for the Inhibition of Human Polymorphonuclear Leukocyte Elastase Via Hydrolysis of
N-t-Boc-alanyl-alanyl-prolyl-alanine-p-nitroanilide (Boc-AAPAN) or
N-t-Boc-alanyl-prolyl-valine-p-nitroanilide (Boc-AAPVN) Reagent 0.05M TES (N-tris[hydroxymethyl]methyl-2-aminoethanesulfonic acid) Buffer, pH 7.5.

0.2 mM Boc-AAPAN or Boc-AAPVN.

To prepare substrate, the solid was first dissolved in 10.0 ml DMSO. Buffer at pH 7.5 was then added to a final volume of 100 ml.

Crude extract of human polymorphonuclear leukocytes (PMN) containing elastase activity.

Inhibitors (azetidinones) to be tested dissolved in DMSO just before use.

To 1.0 ml of 0.2 mM Boc-AAPAN in a cuvette, 0.01–0.1 ml of DMSO with or without inhibitor was added. After mixing, a measurement was taken at 410 mµ to detect any spontaneous hydrolysis due to presence of test compound. 0.05 Milliliters of PMN extract was then added and the ΔOD/min at 410 mµ was measured and recorded. Beckman model 35 spectrophotometer was used.

Results are also expressed as Ki, the micromolar concentration of the inhibitor (µM) giving 50% of the control enzyme activity; or as $k_{obs}/I$ which is the second order rate constant in per mole per second for inactivation of the enzyme.

The elastase activity in the crude PMN extract may vary from one preparation to another. A control of each new batch is run, and the volume added in the assay procedure is adjusted according to activity.

Accordingly, the compounds of Formula A can be used to reduce inflammation and relieve pain in diseases such as emphysema, rheumatoid arthritis, osteoarthritis, gout, bronchial inflammation, atherosclerosis, sepsis, septicemia, shock, periodontitis, cystic fibrosis, infectious arthritis, rheumatic fever and the like.

For treatment of inflammation, fever or pain, the compounds of Formula A may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropymethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadeca-ethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispering or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic monoor diglycerides. In addition, fatty acids such as oleic acid find use in the preparation of injectables.

The compounds of Formula A may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the preparation of the compounds of Formula A and as such are not to be considered as limiting the invention as set forth in the claims appended thereto. Preparation of the starting material 1 may be found in EPO 337,549, published Oct. 18, 1989, which is hereby incorporated by reference.

EXAMPLE 1

(4S)-3,3-Diethyl-1-[(R)-α-n-propyl(4-methyl)-benzylaminocarbonyl]-4-[4-(phenyl(ethoxyphosphinyl)methyl)phenoxy]-azetidin-2-one.

A mixture of (4S)-3,3-diethyl-1-[(R)-α-n-propyl-(4-methyl)-benzylaminocarbonyl]-4-[4-(bromomethyl)-phenoxy]-azetidin-2-one (203 mg, 0.40 mmol) and diethyl phenylphosphonite (155 μL, 0.81 mmol) was heated for 1 hour at 80° C. The desired product was obtained pure after flash chromatography on silica gel using initially 33% ethyl acetate in hexane and subsequently 50% ethyl acetate in hexane as the mobile phase; yield 223 mg (93%); FAB MS m/z 591 (M+1).

EXAMPLE 2

(4S)-3,3-Diethyl-1-[(R)-α-n-propyl(4-methyl)-benzylaminocarbonyl]-4-[4-(phenyl-(hydroxyphosphinyl)-methyl)-phenoxy]-azetidin-2-one The solution of (4S)-3,3-diethyl-1-[(R)-α-n-propyl(4-methyl)-benzylaminocarbonyl]-4-[4-(phenyl(ethoxyphosphinylmethyl)-phenoxy]-azetidin-2-one (165 mg, 0.279 mmol) in methylene chloride (10 mL) was added bromotrimethylsilane (75 μL, 0.568 mmol) with stirring under a nitrogen atmosphere. The reaction mixture was stirred overnight at room temperature and then evaporated. Methanol (10 mL) was added, and the solution was stirred for 1 hour at room temperature. After evaporation, the crude mixture was subjected to flash chromatography on silica gel (packed as a slurry in methylene chloride) using 5% methanol in methylene chloride as the mobile phase. The pure product was obtained as an amorphous glass; yield 86 mg (55%); FAB MS (Li spike): m/z 569 (M+Li), 601 (M+K).

EXAMPLE 3

(4S)-3,3-Diethyl-1-[(R)-α-n-propyl(4-methyl)-benzylaminocarbonyl]-4-[4-(allyl(ethoxyphosphinyl)methyl)phenoxy]-azetidin-2-one This compound was prepared following substantially the same procedure as described in Example 1, but using diethyl allylphosphonite in place of diethyl phenylphosphonite; FAB MS m/z 555 (M+1).

EXAMPLE 4

(4S)-3,3-Diethyl-1-[(R)-α-n-propyl(4-methyl)-benzylaminocarbonyl]-4-[4-(allyl(hydroxyphosphinyl)methyl)phenoxy]-azetidin-2-one This compound was prepared following substantially the same procedure as described in Example 2, but using Example 3 as the starting material; FAB MS m/z 549 (M+Na); 565 (M+K).

EXAMPLE 5

(4S)-3,3-Diethyl-1-[(R)-α-n-propyl(4-methyl)-benzylaminocarbonyl]-4-[4-(methyl(ethoxyphosphinyl)methyl)phenoxy]-azetidin-2-one This compound was prepared following substantially the same procedure as described in Example 1, but using diethyl methylphosphonite in place of diethyl phenylphosphonite; FAB MS m/z 529 (M+1).

EXAMPLE 6

(4S)-3,3-Diethyl-1-[(R)-α-n-propyl(4-methyl)-benzylaminocarbonyl]-4-[4-(methyl(hydroxyphosphinyl)methyl)phenoxy]-azetidin-2-one This compound was prepared following substantially the same procedure as described in Example 2, but using Example 5 as the starting material; FAB MS m/z 523 (M+Na); 539 (M+K).

EXAMPLE 7

(4S)-3,3-Diethyl-1-[(R)-α-n-propyl(4-methyl)-benzylaminocarbonyl]-4-[4-(n-propyl(ethoxyphosphinyl)methyl)-phenoxy]-azetidin-2-one This compound was prepared by catalytic hydrogenation of Example 3 in methanol for 1 hour at atmospheric pressure in the presence of 10% palladium-on-charcoal; FAB MS m/z 557 (M+1).

EXAMPLE 8

(4S)-3,3-Diethyl-1-[(R)-α-n-propyl(4-methyl)-benzylaminocarbonyl]-4-[4-(n-propyl(hydroxyphosphinyl)methyl)-phenoxy]-azetidin-2-one This compound was prepared following substantially the same procedure as described in Example 2, but using Example 7 as the starting material; FAB MS m/z 551 (M+Na); 568 (M+K+1).

EXAMPLE 9

(4S)-3,3-Diethyl-1-[(R)-α-(n-propyl(4-methyl)-benzylaminocarbonyl]-4-[4-(n-propyl(2-methyl-1-ethylcarbonyl-oxy-n-propoxyphosphinyl)methyl)-phenoxy]-azetidin-2-one To a solution of Example 8 (99 mg, 0.187 mmol) in chloroform (1 ml) was added triethylamine (53 μL, 0.375 mmol), 1-chloroisobutyl propionate (46 mg, 0.281 mmol) tetra-n-butylammonium hydrogensulfate (16 mg, 0.047 mmol), and sodium iodide (7 mg, 0.047 mmol). The reaction mixture was stirred in a sealed tapered vial for 2 days at 60° C. The reaction mixture was then evaporated, taken up in a diethyl ether (25 mL) and washed with water. The aqueous layer was extracted with ether and the combined aqueous organic layers were washed with 5% aqueous sodium hydrogencarbonate (3×25 mL), 10% aqueous sodium hydrogensulfite (3×25 mL), saturated aqueous sodium chloride (2×25 mL), dried (magnesium sulfate), and evaporated. The product was purified by flash silica gel chromotography using initially 30% ethyl acetate/hexane and subsequently 50% ethyl acetate/hexane as eluent; yield 44 mg (36%); FAB MS m/z 679 (M+Na).

What is claimed is:

1. A compound Formula (A)

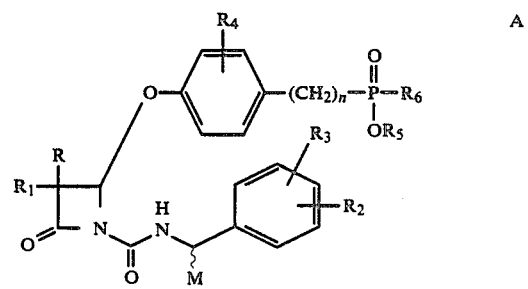

or a pharmaceutically acceptable salt thereof wherein:

R is H, $C_{1-6}$ alkyl, or $C_{2-6}$ alkenyl;

$R_1$ is H, $C_{1-6}$ alkyl, $C_{2-6}$ alkenyl or $C_{1-6}$ alkoxy-$C_{1-6}$ alkyl;

M is
- (1) hydrogen,
- (2) $C_{1-6}$ alkyl,
- (3) hydroxy $C_{1-6}$-alkyl,
- (4) halo $C_{1-6}$-alkyl,
- (5) $C_{2-6}$ alkenyl, or
- (6) $C_{1-6}$ alkoxy-$C_{1-6}$ alkyl;

$R_2$ and $R_3$ are each independently
- (1) hydrogen,
- (2) $C_{1-6}$ alkyl,
- (3) halo,
- (4) carboxy,
- (5) $C_{1-6}$ alkoxy,
- (6) phenyl,
- (7) $C_{1-6}$ alkylcarbonyl,
- (8) $C_{1-6}$ alkyloxycarbonyl,
- (9) di-($C_{1-6}$alkyl)amino,
- (10) phenoxy, or $R_2$ and $R_3$ are joined together with the carbon atoms to which they are attached to form a ring selected from furan, thiophene, and dioxacyclopentane;

$R_4$ is
- (a) hydrogen,
- (b) $C_{1-6}$ alkyl,
- (c) halo, or
- (d) $C_{1-6}$ alkoxy;

n is 0, 1, 2, 3, or 4;

$R_5$ is
- (1) Hydrogen,
- (2) $C_{1-6}$ alkyl,
- (3) $C_{6-10}$ aryl wherein the aryl group is selected from the group consisting of
  - (a) phenyl,
  - (b) naphthyl,
  - (c) pyridyl,
  - (d) furyl,
  - (e) pyrryl,
  - (f) thienyl,
  - (g) imidazolyl,
  - (h) benzimidazolyl,
  - (i) pyrazinyl,
  - (j) pyrimidyl,
  - (k) quinolyl,
  - (l) isoquinolyl,
  - (m) benzofuryl, and
  - (n) benzothienyl, and mono and di-substituted $C_{6-10}$ aryl as defined above in items (a) to (n) wherein the substituents are independently $C_{1-6}$ alkyl, halo, hydroxy, $C_{1-6}$ alkyloxy, $C_{1-6}$ alkylcarbonyl, or $C_{1-6}$ alkoxy $C_{1-6}$ alkyl;
- (4) $C_{1-6}$ alkylcarbonyloxy-$C_{1-6}$ alkyl;

$R_6$ is
- (a) hydrogen,
- (b) $C_{1-6}$ alkyl,
- (c) $C_{2-6}$ alkenyl,
- (d) substituted $C_{1-6}$ alkyl wherein the substituent is halo, hydroxy, $C_{1-6}$ alkoxy, $C_{1-6}$ alkylcarbonyloxy, amino, $C_{1-6}$ alkylamino, or di-($C_{1-6}$ alkyl)amino,
- (e) $C_{6-10}$ aryl wherein the aryl group is selected from the group consisting of
  - (1) phenyl,
  - (2) naphthyl,
  - (3) pyridyl,
  - (4) furyl,
  - (5) pyrryl,
  - (6) thienyl,
  - (7) imidazolyl,
  - (8) benzimidazolyl,
  - (9) pyrazinyl,
  - (10) pyrimidyl,
  - (11) quinolyl,
  - (12) isoquinolyl,
  - (13) benzofuryl, and
  - (14) benzothienyl, and mono and di-substituted $C_{6-10}$ aryl as defined above in items (1) to (14) wherein the substituents are independently $C_{1-6}$ alkyl, halo, hydroxy, $C_{1-6}$ alkyloxy, $C_{1-6}$ alkylcarbonyl, and $C_{1-6}$ alkoxycarbonyl.

2. A compound of Formula A according to claim 1, wherein $R_5$ is
- (1) Hydrogen,
- (2) $C_{1-6}$ alkyl,
- (3) $C_{6-10}$ aryl wherein the aryl group is selected from the group consisting of
  - (a) phenyl,
  - (b) pyridyl,
  - (c) furyl,
  - (d) thienyl,
  - (e) imidazolyl,
  - (f) benzimidazolyl,
  - (g) pyrimidyl,
  - (h) benzofuryl, and
  - (i) benzothienyl, or
- (4) $C_{1-6}$ alkylcarbonyloxy-$C_{1-6}$ alkyl.

3. A compound of Formula A according to claim 2, wherein $R_6$ is
- (a) hydrogen,
- (b) $C_{1-6}$ alkyl,
- (c) $C_{2-6}$ alkenyl,
- (d) substituted $C_{1-6}$ alkyl wherein the substituent is halo, hydroxy, $C_{1-6}$ alkoxy, $C_{1-6}$ alkylcarbonyloxy, amino, $C_{1-6}$ alkylamino, or di-($C_{1-6}$ alkyl)-amino,
- (e) $C_{6-10}$ aryl wherein the aryl group is selected from the group consisting of
  - (1) phenyl,
  - (2) pyridyl,
  - (3) furyl,
  - (4) thienyl,
  - (6) imidazolyl,
  - (7) benzimidazolyl,
  - (8) pyrimidyl,
  - (9) benzofuryl, and
  - (10) benzothienyl.

4. A compound of Formula A according to claim 3, wherein $R_5$ is
- (1) Hydrogen,
- (2) $C_{1-6}$ alkyl,
- (3) substituted $C_{6-10}$ aryl wherein the aryl group is selected from the group consisting of
  - (a) phenyl,
  - (b) thienyl,
  - (d) benzofuryl, and
  - (f) benzothienyl, or
- (4) $C_{1-6}$ alkylcarbonyloxy-$C_{1-6}$ alkyl.

5. A compound of Formula A according to claim 4, wherein
R$_6$ is
(a) hydrogen,
(b) C$_{1-6}$ alkyl,
(c) C$_{2-6}$ alkenyl,
(d) C$_{6-10}$ aryl wherein the aryl group is selected from the group consisting of
(1) phenyl,
(2) thienyl,
(3) isothiazolyl,
(4) benzofuryl,
(5) isobenzofuryl, and
(6) benzothienyl.

6. A compound of Formula A according to claim 5, wherein
M, R, and R$_1$ are each independently C$_{1-6}$ alkyl or C$_{2-6}$ alkenyl;
R$_2$ and R$_3$ are each independently hydrogen, C$_{1-6}$ alkyl, C$_{1-6}$ alkoxy, or R$_2$ and R$_3$ are joined together with the carbon atoms to which they are attached to form a ring selected from furan, thiophene, or dioxacyclopentane;
R$_4$ is hydrogen, C$_{1-6}$ alkyl, fluoro or chloro;
n is 0 or 1;
R$_5$ is hydrogen, C$_{1-6}$ alkyl, C$_{1-6}$-alkylcarbonyloxy-C$_{1-6}$ alkyl; and
R$_6$ is hydrogen, C$_{1-6}$ alkyl, C$_{2-6}$ alkenyl or C$_{6-10}$aryl.

7. A compound according to claim 6 of Formula A wherein
M, R and R$_1$ are each independently C$_{1-6}$ alkyl;
R$_2$ is hydrogen, and
R$_3$ is C$_{1-6}$ alkyl, C$_{1-6}$ alkyloxy, or
R$_2$ and R$_3$ are joined together with the carbon atoms to which they are attached to form a ring selected from furan or dioxacyclopentane;
R$_4$ is hydrogen, C$_{1-6}$ alkyl, fluoro, or chloro;
n is 0 or 1;
R$_5$ is hydrogen, C$_{1-6}$ alkyl or C$_{1-6}$-alkylcarbonyloxy-C$_{1-6}$ alkyl;
R$_6$ is hydrogen, C$_{1-6}$ alkyl, C$_{2-6}$ alkenyl or C$_{6-10}$aryl.

8. A compound according to claim 7 wherein
M is n-propyl;
R and R$_1$, are ethyl;
n is 0 or 1;
R$_2$ is hydrogen or C$_{1-6}$ alkyl, and
R$_3$ is methyl, or methoxy, or R$_2$ and R$_3$ are joined together with the carbon atoms to which they are attached to form a ring selected from furan or dioxacyclopentane;
R$_5$ is hydrogen, C$_{1-6}$ alkyl or C$_{1-6}$-alkylcarbonyloxy-C$_{1-6}$ alkyl; and
R$_6$ is hydrogen, methyl, ethyl, allyl, or phenyl.

9. A compound of Formula A according to claim 8 selected from the group consisting of
(a) (4S)-3,3-Diethyl-1-[(R)-α-n-propyl(4-methyl)benzylaminocarbonyl]-4-[4-(phenyl(hydroxyphosphinyl)methyl)-phenoxy]azetidin-2-one;
(b) (4S)-3,3-Diethyl-1-[(R)-α-n-propyl(4-methyl)benzylaminocarbonyl]-4-[4-(allyl(ethoxyphosphinyl)methyl)-phenoxy]azetidin-2-one;
(c) (4S)-3,3-Diethyl-1-[(R)-α-n-propyl-(4-methyl)benzylaminocarbonyl]-4-[4-(methyl(ethoxyphosphinyl)methyl)-phenoxy]azetidin-2-one;
(d) (4S)-3,3-Diethyl-1-[(R)-α-n-propyl(4-methyl)-benzylaminocarbonyl]-4-[4-(phenyl(ethoxyphosphinyl)methyl)-phenoxy]azetidin-2-one;
(e) (4S)-3,3-Diethyl-1-[(R)-α-n-propyl(4-methyl)-benzylaminocarbonyl]-4-[4-(allyl(hydroxyphosphinyl)methyl)-phenoxy]azetidin-2-one;
(f) (4S)-3,3-Diethyl-1-[(R)-α-n-propyl(4-methyl)-benzylaminocarbonyl]-4-[4-(methyl(hydroxyphosphinyl)methyl)-phenoxy]azetidin-2-one;
(g) (4S)-3,3-Diethyl-1-[(R)-α-n-propyl(4-methyl)-benzylaminocarbonyl]-4-[4-(n-propyl(ethoxyphosphinyl)methyl-phenoxy]azetidin-2-one;
(h) (4S)-3,3-Diethyl-1-[(R)-α-n-propyl(4-methyl)benzylaminocarbonyl]-4-[4-(n-propyl(hydroxyphosphinyl)-phenoxy]azetidin-2-one; and
(i) (4S)-3,3-Diethyl-1-[(R)-α-n-propyl(4-methyl)benzylaminocarbonyl]-4-[4-(n-propyl-(2-methyl-1-ethylcarbonyloxy-n-propoxyphosphinyl)methyl)-phenoxy]azetidin-2-one.

10. A pharmaceutical composition for the inhibition of leukocyte elastase which comprises a nontoxic therapeutically effective amount of a compound of claim 1, and a pharmaceutically acceptable carrier.

11. A pharmaceutical composition for the inhibition of leukocyte elastase which comprises a nontoxic therapeutically effective amount of a compound of claim 9 and a pharmaceutically acceptable carrier.

12. A method of treatment for the inhibition of human leukocyte elastase which comprises the administration to a subject in need of such inhibition a nontoxic therapeutically effective amount of a compound of claim 1.

13. A method of treatment for the inhibition of human leukocyte elastase which comprises the administration to a subject in need of such inhibition a nontoxic therapeutically effective amount of a compound of claim 9.

* * * * *